United States Patent
Guerin et al.

(10) Patent No.: US 6,336,928 B1
(45) Date of Patent: Jan. 8, 2002

(54) DEVICE FOR SECURING AT LEAST TWO VERTEBRAE

(75) Inventors: Jean Guerin, Hospital Pellegrin - Place Amèlie Raba Lèon, 33000 Bordeaux (FR); Roger Robert, CHU Laënnec Nuerochirurgie, Nantes (FR), 44000; Michel Tremoulet, CHU Purpan Place du Docteur Baylac, Toulouse (FR), 31300; Philippe Jourdan, Clinique Residence du Parc - Rue, Gaston Berger Marseilles (FR), 13010; François San Galli, Raba Lèon (FR); Bertrand Gauneau, Roanne (FR)

(73) Assignees: Depuy France, Villeurbanne; Jean Guerin, Bordeaux; Roger Robert, Nantes; Michel Tremoulet, Toulouse; Philippe Jourdan, Marseille; Francois San Galli, Bordeaux, all of (FR)

( * ) Notice: Subject to any disclaimer, the term of this patent is extended or adjusted under 35 U.S.C. 154(b) by 0 days.

(21) Appl. No.: 09/284,569

(22) PCT Filed: Oct. 17, 1997

(86) PCT No.: PCT/FR97/01866

§ 371 Date: Sep. 10, 1999

§ 102(e) Date: Sep. 10, 1999

(87) PCT Pub. No.: WO98/17189

PCT Pub. Date: Apr. 30, 1998

(Under 37 CFR 1.47)

(30) Foreign Application Priority Data

Oct. 18, 1996 (FR) .............................................. 9612951

(51) Int. Cl.$^7$ .............................................. A61B 17/70
(52) U.S. Cl. .......................................... 606/61; 606/60
(58) Field of Search ........................... 623/17.11, 17.16; 606/60, 61, 69, 63, 66

(56) References Cited

U.S. PATENT DOCUMENTS

| 4,047,524 | A | * | 9/1977 | Hall ............................. 606/61 |
| 4,269,180 | A | * | 5/1981 | Dall et al. .................... 606/69 |
| 5,246,443 | A | * | 9/1993 | Mai .............................. 606/78 |
| 5,360,430 | A | * | 11/1994 | Lin ............................... 606/61 |
| 5,395,372 | A | * | 3/1995 | Holt et al. .................... 606/61 |
| 5,660,188 | A | * | 8/1997 | Groiso ........................ 129/898 |
| 5,674,296 | A | * | 10/1997 | Bryan et al. ................. 623/17 |
| 5,713,899 | A | * | 2/1998 | Holt et al. .................... 606/61 |

FOREIGN PATENT DOCUMENTS

| EP | 0 646 353 | 4/1995 |
| EP | 0 667 127 | 8/1995 |
| FR | 2 694 696 | 2/1994 |
| FR | 2 709 410 | 3/1995 |

* cited by examiner

Primary Examiner—Gene Mancene
Assistant Examiner—Michael B. Priddy
(74) Attorney, Agent, or Firm—Young & Thompson

(57) ABSTRACT

Device for joining at least two vertebral bodies, which comprises at least one plate (1) equipped at each end with anchoring parts (1*a*) (1*b*) which can be introduced substantially vertically into seats previously established in the vertebral bodies to be joined, and then, after introduction, can be folded back at an angle towards one another in order to exert a constant compression of the vertebral bodies and to ensure perfect anchoring, wherein each anchoring part (1*a*) and (1*b*) is connected to the ends of the corresponding plate via a central connection zone (1*c*) (1*d*) delimiting two profiled notches (1*c*1) (1*d*1) (1*c*2) (1*d*2) in order to permit deformation of the zone, in such a way that each pair of anchoring parts permits a compression, both at the level of the plate and at the level of its ends, and in such a way that the anchoring parts at each end of the plate permit a clamping which prevents any extraction.

11 Claims, 3 Drawing Sheets

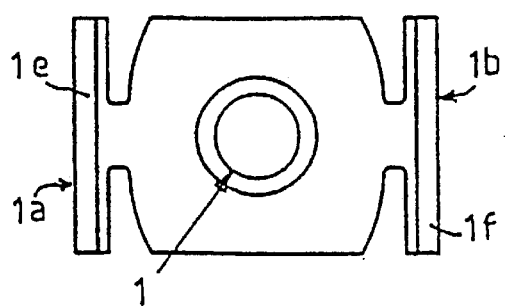
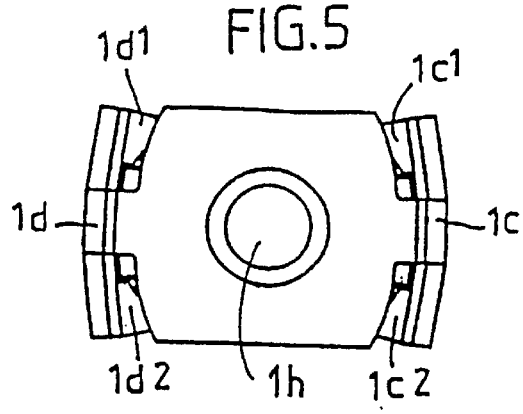
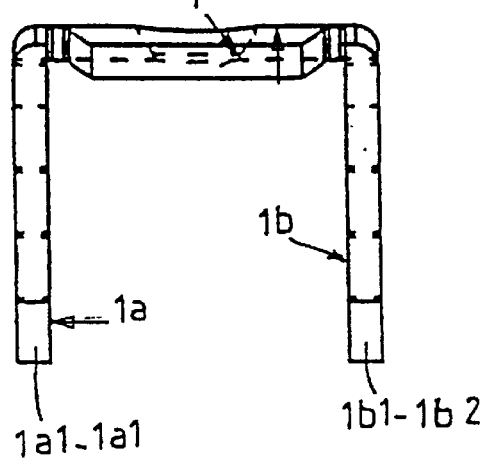
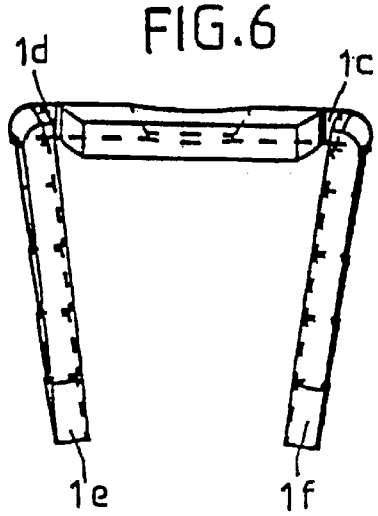

DEVICE FOR SECURING AT LEAST TWO VERTEBRAE

The invention concerns the technical sector of orthopaedic implants, in particular implants for the cervical spine.

It is known that degeneration of a cervical disc between two vertebrae causes the disc to slip, which generally results in neuromuscular problems after a nerve root of the spinal column becomes trapped. In attempting to overcome these problems, different types of implants have been proposed which may or may not allow the mobility of the vertebrae in question to be preserved. More particularly, the invention relates to implants effecting arthrodesis of the vertebrae.

Among these known solutions, mention may be made of intersomatic cages, intercervical prostheses and rigid mechanical devices which essentially employ a plate and screws.

In the latter case, the plate is positioned on the anterior face of the vertebral bodies to be joined, the screws being engaged through the plate so as to be screwed into a part of the vertebral bodies with a view ensuring that the fixture is held securely in place. It should be noted that a graft can be arranged between the two vertebral bodies, the function of which graft is to ensure mechanical support until bone fusion between the two vertebral bodies takes place. The plate therefore ensures that the graft is held in place and serves as a prop or stiffening element between the two vertebral bodies.

It should be noted, however, that this fixture is relatively complex and its use requires a certain degree of dexterity. Furthermore, it does not allow a constant compression force to be exerted throughout the phase of fusion in order to reduce the healing time.

It has also already been proposed, for example in U.S. Pat. No. 5,395,372, to use arthrodesis plates comprising pointed branches which are intended to be impacted in the vertebral bodies and whose geometry, appropriately inclined, makes it possible to ensure a certain compression force caused by the impaction. These plates are held in place by means of screws. These solutions are unsatisfactory, however.

A retaining clamp for osteosynthesis has also been described in FR-A-2 694 696, made of a shape-memory material and comprising two branches and a crosspiece, it being possible for the branches to be introduced in a rectilinear manner into drill holes before they deform in order to apply compression when the temperature of the clamp recovers the body temperature. Likewise, in application EP-A-0 646 353, it has already been proposed to use clamps made of wire folded back in such a way as to form a plurality of branches which are able to close together by means of a deformation of a shape-memory alloy.

Since the clamp is made of wire, the compression forces or clamping forces possible are dependent on complex processes for obtaining the shape memory, and the restoring forces of the different branches are difficult to manage.

The object of the invention is to overcome these disadvantages in a simple, reliable, effective and economical manner.

The problem which the invention proposes to solve is that of providing arthrodesis of the vertebrae by means of a single compact element which is able to afford constant compression between the vertebral bodies in question and to keep such pressure constant, particularly in the area of the spongy bone.

Furthermore, the compact element, which is intended to be put in place via an anterior approach to the cervical spine, in order generally to maintain a position of lordosis, easily risks being extracted unless, as in the prior art, it is fixed by means of screws. The object of the invention is to ensure, without using complementary securing means such as screws, a perfect holding in place of the clamp, even in the case of physiological movement reducing the lordosis effect.

To solve such a problem, a device has been designed and developed for joining at least two vertebral bodies, characterized in that it comprises at least one plate equipped at each end with a pair of anchoring parts which can be introduced substantially vertically, that is to say axially, into parallel seats previously established in the vertebral bodies to be joined, and then, after introduction, can be folded back at an angle towards one another in order to exert a constant compression of the vertebral bodies and to ensure perfect anchoring.

To solve the problem of facilitating the positioning of the plate while at the same time permitting an automatic compression after impaction, each plate and its anchoring parts are made from a shape-memory material, which shape corresponds to a defined and stable geometric shape at a positive temperature and to another geometric shape at a negative temperature.

At very substantially 0° C. the anchoring parts are arranged in a substantially vertical plane, whereas at a positive temperature of very substantially 37° C. the said parts are automatically folded back and in. It should be noted that the plates are stored at 0° C. in a form allowing the anchoring parts to maintain the vertical position.

To solve the problem of permitting deformation of the anchoring parts after impaction, each anchoring part is connected to the ends of the corresponding plate via a central connection zone delimiting two profiled notches in order to permit the deformation of the said parts.

Advantageously, each anchoring part comprises two tabs which are connected at one of their ends via a common branch which comprises the central connection zone.

It will thus be understood that when the plate recovers body temperature, the anchoring parts in the form of tabs can thus tilt at an angle in a sagittal plane in order to exert a permanent compression on the spongy bone of the vertebral bodies of the vertebrae in question, each time around the central connection zone, whilst the two tabs situated on one and the same central connection zone can tilt towards one another by virtue of the presence of the notches, so as to deform in a frontal plane and more precisely close to the horizontal in such a way as to converge, which prevents the extraction of the plate.

The compression force exerted by the two pairs of anchoring tabs and tending to bring two vertebrae closer to one another can be maintained at a value significantly greater than the force tending to bring two tabs of one and the same pair closer to one another at an angle. This can be easily achieved on account of the fact that the central connection zone can have a considerable amount of material subjected to the memory effect whilst the closing together of the two tabs of a single pair can be determined by the smaller amount of material in the area of the notch at the location where the tab joins the central connection zone.

To solve the problem of ensuring perfect anchoring, each tab has on the inside a series of toothed spikes.

The invention is also distinguished by the following characteristics:

the plate has a transverse curvature corresponding very substantially to the anterior face of the vertebral bodies;

the plate has at least one slot for the engagement of one or more securing screws. This slot is preferably a central slot, which can advantageously be circular. It can be internally threaded or otherwise configured so as to receive an element of an ancillary intended to support the plate when it is at its lowered temperature in order to keep it and present it in a well defined position. This passage can additionally be used for the insertion of a spacing element, such as an intersomatic cage or a bone graft or another material intended to facilitate arthrodesis. Finally, particularly in the case of a plate intended to join two vertebrae on either side of a central vertebra, this passage can be used to receive a screw which is screwed into the body of the central vertebra and thereby to ensure effective joining of the three vertebrae with compression of the end vertebrae against the intermediate vertebra.

The plate according to the invention can also have, half way between the two pairs of anchoring parts or tabs, intersomatic reliefs which are intended to penetrate into the intervertebral space upon positioning of the plate and to maintain the height of the articular midline.

The invention is explained in greater detail below with reference to the attached drawings, in which:

FIG. 3 is a plan view of the plate at the 0° C. state.

FIG. 4 is a front view corresponding to FIG. 3.

FIG. 5 is a plan view of the plate at the 37° C. state.

FIG. 6 is a front view corresponding to FIG. 5.

As has been indicated, the problem which the invention proposes to solve is that of ensuring a constant compression of the vertebral bodies (V1) and (V2) of the vertebrae which are to be joined. To this end, the joining device according to the invention comprises a compact connection element comprising a plate (1) equipped at each end with anchoring parts in the form of tabs (1a) and (1b). These anchoring parts (1a) and (1b) are designed to be engaged in seats previously established in the vertebral bodies to be joined (V1) and (V2), opposite the spinous processes.

Figure 1:
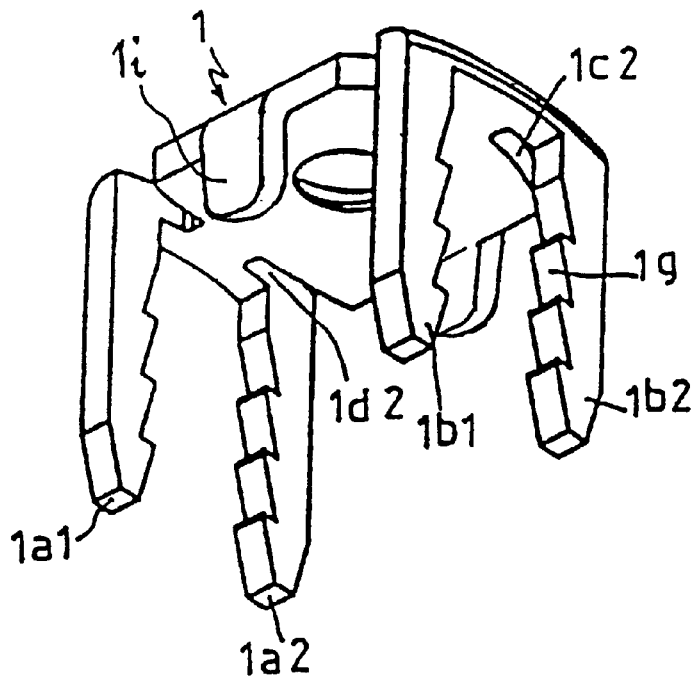
FIG. 1 is a perspective view of the overall plate at a temperature of about 0° C.

The plate (1) and its anchoring parts (1a) and (1b) are made from a shape-memory material in order to correspond to a defined and stable geometric shape at a positive temperature of about 37° C. and to another geometric shape at a much lower temperature of about 0° C. More particularly, at a temperature of about 0° C., the anchoring parts (1a) and (1b) are arranged in a substantially vertical plane (FIGS. 1, 3 and 4). In this state, it is possible to introduce the anchoring parts (1a) (1b) into the corresponding arrangements previously established in the vertebral bodies. These arrangements preferably consist of holes drilled in the vertebral bodies and advantageously having a diameter significantly greater than the space taken up by the tabs in such a way as to prevent wedging on the cortical bone and, consequently, to permit perfect clamping of the spongy bone.

By contrast, at the temperature of about 37° C., the anchoring parts (1a) and (1b) are automatically folded back and in, at an angle towards one another, in order to exert, concomitantly, a constant compression of the vertebral bodies (V1) and (V2) while ensuring perfect anchoring of the plate (1). At the same time, the two clamping tabs (1a) of one and the same pair fold back at an angle towards one another, as can be seen in particular in FIG. 5, so that not only is there the compression effect by means of the tabs moving in a sagittal plane, but there is also a pinching effect by means of the tabs which, moving in a horizontal plane, close together and, in these oblique positions, prevent any inadvertent extraction of the plate.

In order to permit this change of geometric shape by the effect of increasing the temperature, each anchoring part (1a) and (1b) is connected to the ends of the plate (1) via a central connection zone (1c) and (1d) delimiting two profiled notches (1c1) (1c2) and (1d1) (1d2). Each anchoring part (1a) and (1b) comprises two tabs (1a1) (1a2) and (1b1) (1b2) which are connected at one of their ends via a common branch (1e) (1f) which is itself integral with the central connection zone (1c) (1d).

Figure 2:
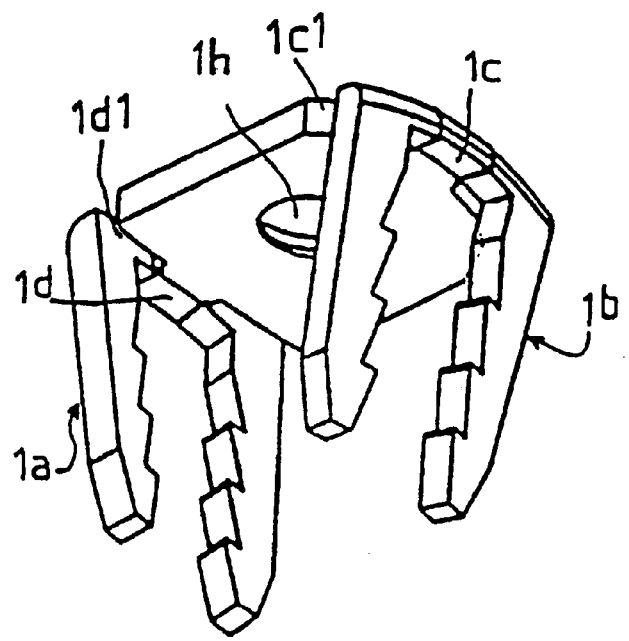
FIG. 2 is a perspective view corresponding to FIG. 1 at a positive temperature of 37° C.
Figure 7:
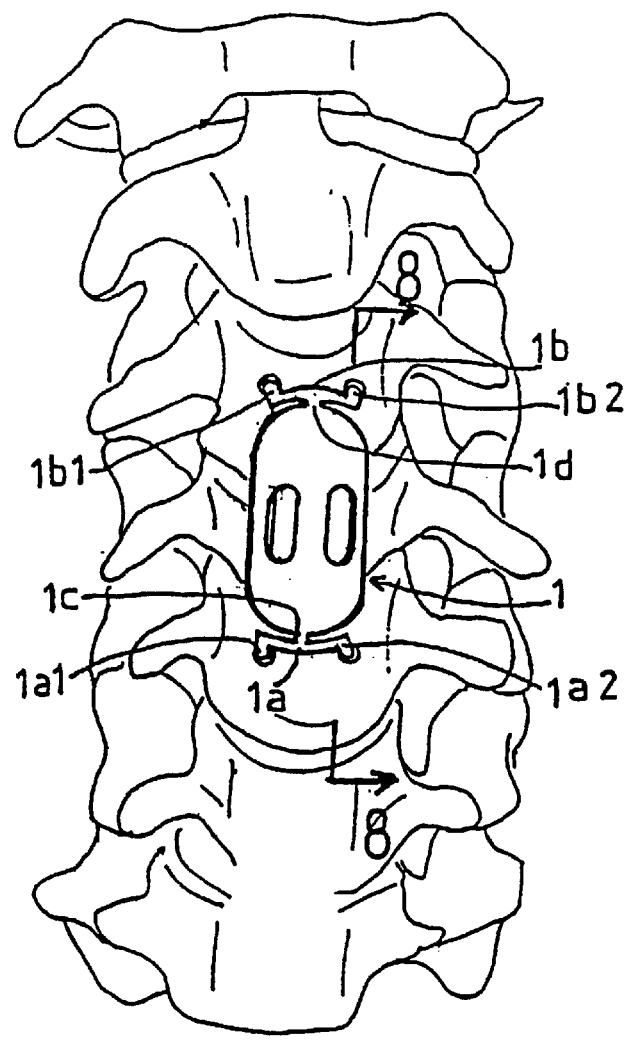
FIG. 7 is a front view of part of the spinal column showing the arthrodesis of two vertebral bodies according to the characteristics of the invention.
Figure 8:
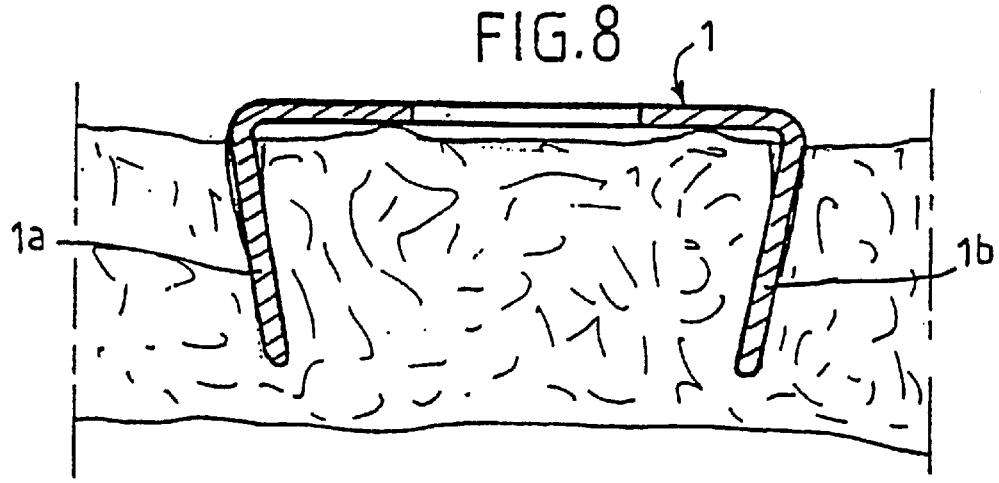
FIG. 8 is a longitudinal cross section corresponding to FIG. 7.

Given the design of each anchoring part, their deformation, under the effect of temperature variation under the conditions indicated above, has the effect of deforming each of the tabs (1a1) (1a2) and (1b1) (1b2) both in the frontal plane and in the sagittal plane (FIGS. 2, 5 and 6). The result of this is that this deformation, under the conditions indicated, of each of the tabs permits a compression both in the area of the plate and in the area of its ends, in order to have a closing together of cortical and spongy bone.

As will be seen, the anchoring tabs (1a, 1b) are situated a certain distance from their central connection zone (1c, 1d) by means of the interposition of a bridge of material defining a part of the edge of the corresponding notch and this bridge of material can be used to adjust the force or value of the deformation which brings the two tabs of one and the same pair closer to one another at an angle, for example the tabs (1a) when the positive temperature is reached, the desired blocking clamping between the two tabs of one and the same pair being generally less than the compression clamping of the vertebral bodies against one another ensured by the closing together at an angle of the two pairs of tabs (1a) and (1b).

Each tab (1a1) (1a2) and (1b1) (1b2), whose ends are blunt, has on the inside a series of toothed spikes (1g). The plate (1) has a transverse curvature corresponding very substantially to the profile of the anterior face of the vertebral bodies and a longitudinal curvature for adapting to the cervical lordosis. The length of the plate (1) depends on the number of vertebral bodies to be joined.

The advantages are clear from the description, and in particular we underline and reiterate the possibility of maintaining a constant pressure, both in the area of the spongy bone and in the area of the cortical bone, by the automatic deformation of the anchoring parts under the effect of increasing the temperature.

It should be noted that each plate, together with its anchoring parts, is stored at 0° C. or at a negative temperature, in a form permitting the said anchoring parts to be maintained in a vertical position. The plate assembly is easily put into place using an ancillary with which it is possible to make the four seats which will receive the four tabs (1a1) (1a2) and (1b1) (1b2). The ancillary can advantageously be fixed, for example by screwing, in a passage or slot (1h).

As is represented in FIG. 1, the plate (1) can also comprise reliefs (1i) between the pairs of tabs (1a) (1b), for example of the order of 5 mm in length and 4 mm in width, extending parallel to the tabs and intended to be introduced between two vertebral bodies upon positioning of the plate, in order to maintain a certain value of the disc space and to relieve the intervertebral disc.

The plate can be made in one piece by cutting out and folding or by stamping from a sheet of metal, for example nickel titanium, which can be trained by virtue of its shape-memory properties.

What is claimed is:

1. Device for joining at least two vertebral bodies, which comprises at least one plate (1) equipped at each end with anchoring parts (1a) (1b) which can be introduced substantially vertically into seats previously established in the vertebral bodies to be joined, and then, after introduction, can be folded back at an angle towards one another in order to exert a constant compression of the vertebral bodies and to ensure perfect anchoring, wherein each anchoring part (1a) and (1b) is connected to the ends of the corresponding plate via a central connection zone (1c) (1d) delimiting two profiled notches (1c1) (1d1) (1c2 (1d2) in order to permit deformation of the said zone, in such a way that each pair of anchoring parts permits a compression, both at the level of the plate and at the level of its ends, and in such a way that the anchoring parts at each end of the plate permit a clamping which prevents any extraction.

2. Device according to claim 1, wherein each plate (1) and its anchoring parts (1a) and (1b) are made from a shape-memory material, which shape corresponds to a defined and stable geometric shape at body temperature and to another geometric shape at a temperature substantially lower than body temperature.

3. Device according to claim 2, wherein at said lower temperature the anchoring parts (1a) and (1b) are arranged in a substantially vertical plane, whereas at body temperature the said parts are folded back and in.

4. Device according to claim 2, which is made in one piece by being cut out from a metal plate and then treated shape memory.

5. Device according to claim 1, wherein the plate (1) has a transverse curvature corresponding to a face of a vertebral body and a longitudinal curvature for adapting to a cervical lordoses.

6. Device according to claim 1, wherein the plate (1) has at least one slot (1h).

7. Device according to claim 6, wherein the said slot is designed or threaded for securing to a positioning ancillary.

8. Device according to claim 1, wherein the plate (1) has intersomatic reliefs (1i) between the pairs of anchoring parts.

9. Device for joining at least two vertebral bodies, which comprises at least one plate (1) equipped at each end with anchoring parts (1a) (1b) which can be introduced substantially vertically into seats previously established in the vertebral bodies to be joined, and then, after introduction, can be folded back at an angle towards one another in order to exert a constant compression of the vertebral bodies and to ensure perfect anchoring, wherein each anchoring part (1a) and (1b) is connected to the ends of the corresponding plate via a central connection zone (1c) (1d) delimiting two profiled notches (1c1) (1d) (1c2 (1d2) in order to permit deformation of the said zone, in such a way that each pair of anchoring parts permits a compression, both at the level of the plate and at the level of its ends, and in such a way that the anchoring parts at each end of the plate permit a clamping which prevents any extraction, and wherein the anchoring parts (1a) (1b) comprise tabs (1a1) (1a2) (1b1) (1b2) which are connected at one of their ends via a common branch (1e) (1f) which comprise a central connection zone (1c) (1d).

10. Device according to claim 9, wherein each tab (1a1) (1a2) (1b1) (1b2) has on the inside a series of toothed spikes (1g).

11. Device according to claim 9, the tabs each having a series of toothed spikes thereon, said spikes of each tab of each pair extending toward said spikes of the other tab of said pair of tabs.

* * * * *